United States Patent
Erickson et al.

(10) Patent No.: US 7,138,529 B2
(45) Date of Patent: Nov. 21, 2006

(54) SUBSTITUTED 3-CYANOTHIOPHENE ACETAMIDES AS GLUCAGON RECEPTOR ANTAGONISTS

(75) Inventors: Shawn David Erickson, Leonia, NJ (US); Paul Gillespie, Westfield, NJ (US); Kevin Richard Guertin, Verona, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 414 days.

(21) Appl. No.: 10/820,900

(22) Filed: Apr. 8, 2004

(65) Prior Publication Data
US 2004/0209943 A1 Oct. 21, 2004

Related U.S. Application Data

(60) Provisional application No. 60/463,200, filed on Apr. 16, 2003.

(51) Int. Cl.
C07D 409/00 (2006.01)
C07D 333/38 (2006.01)
A61K 31/38 (2006.01)

(52) U.S. Cl. .......... 549/61; 549/59; 514/447; 514/444

(58) Field of Classification Search .......... 549/61, 549/59; 514/438, 444, 447
See application file for complete search history.

(56) References Cited

U.S. PATENT DOCUMENTS

| 5,206,375 | A | * | 4/1993 | Schefczik et al. .......... 548/152 |
| 5,672,718 | A | * | 9/1997 | Fischer et al. ............... 549/28 |
| 5,981,567 | A | * | 11/1999 | Fischer et al. ............... 514/409 |
| 6,479,489 | B1 | * | 11/2002 | Fischer et al. ............... 514/235.5 |
| 6,555,567 | B1 | * | 4/2003 | Fischer et al. ............... 514/409 |
| 6,774,133 | B1 | * | 8/2004 | Fischer et al. ............... 514/278 |
| 2004/0097552 | A1 | | 5/2004 | Duffy et al. |

FOREIGN PATENT DOCUMENTS

| WO | WO 98/40385 A1 | 9/1998 |
| WO | WO 99/46267 A1 | 9/1999 |
| WO | WO 00/14090 A1 | 3/2000 |
| WO | WO 2004/024065 | 3/2004 |
| WO | WO 2004/024066 | 3/2004 |

OTHER PUBLICATIONS

Interchim Intermediates, XP002292047 (2002).
Ambinter Screening Library, XP002292048 (2004).

* cited by examiner

Primary Examiner—Deborah C. Lambkin
(74) Attorney, Agent, or Firm—George W. Johnston; Patricia S. Rocha-Tramaloni; Brian C. Remy

(57) ABSTRACT

The present invention relates to compounds of formula (I)

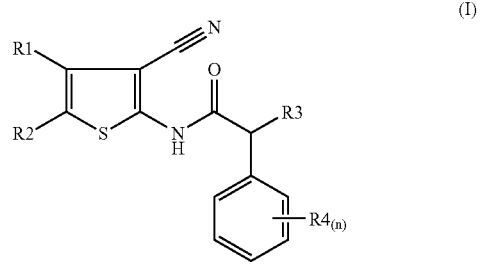

wherein R1, R2, R3, R4 and n are as defined in the description and claims, and pharmaceutically acceptable salts thereof. The compounds are useful for the treatment and/or prophylaxis of diseases which are associated with the antagonism of the glucagon receptor, such as diabetes.

36 Claims, No Drawings

SUBSTITUTED 3-CYANOTHIOPHENE ACETAMIDES AS GLUCAGON RECEPTOR ANTAGONISTS

PRIORITY TO PROVISIONAL APPLICATION(S) UNDER 35 U.S.C. § 119(E)

This application claims priority under 35 U.S.C. § 119(e) of provisional application(s) Ser. No. 60/463,200, filed on Apr. 16, 2003.

BACKGROUND OF THE INVENTION

The present invention is concerned with novel substituted 3-cyanothiophene acetamides, their manufacture and their use as medicaments. The present invention further relates to pharmaceutically acceptable salts of these 3-cyanothiophene compounds and pharmaceutical compositions containing these compounds.

The glucagon receptor (GLUR) is a G-protein coupled 7-transmembrane domain receptor (GPCR) of the secretin family. When the natural hormonal ligand glucagon binds to the GLUR, there is an activation of adenylate cyclase and a concomitant increase in cAMP production. This increase in cAMP causes an activation of glycogen phosphorylase resulting in an increase in hepatic glucose production. The actions of glucagon are counter-regulatory to insulin and thus it is believed to play a central role in glucose homeostasis. Glucagon has been used clinically to rescue diabetic patients from hypoglycemia. Thus, a small molecule GLUR antagonists has considerable potential for the treatment of diabetes.

SUMMARY OF THE INVENTION

Briefly stated, novel substituted 3-cyanothiophene acetamides have been found to be glucagon receptor antagonists that inhibit glucagon stimulated increase in cAMP production in a functional cell based assay. Consequently, the compounds of the present invention are useful for the treatment and/or prophylaxis of diabetes, and/or impaired glucose tolerance, as well as other conditions wherein the antagonism of the glucagon receptor gives a therapeutic benefit.

According to one aspect of the present invention, there is provided a compound of formula (I)

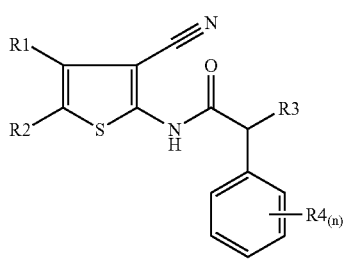

(I)

wherein R1, R2, R3, R4 and n are as defined below.

According to another aspect of the present invention, there is provided a pharmaceutical composition comprising a compound of formula (I), or pharmaceutically acceptable salts thereof, and a pharmaceutically acceptable carrier and/or adjuvant.

According to a further aspect of the present invention, there is provided a method for treating or preventing diseases which are associated with antagonism of the glucagon receptor, comprising administering to a patient in need thereof, a therapeutically effective amount of a compound of formula (I).

These and other features, aspects and advantages of the present invention will become better understood with reference to the following drawings, description and claims.

DETAILED DESCRIPTION OF THE INVENTION

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, preferably to fluorine and chlorine.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

Alkyl groups can optionally be substituted e.g. with halogen, hydroxy, lower-alkoxy, lower-alkoxy-carbonyl, $NH_2$, N(H, lower-alkyl) and/or N(lower-alkyl)$_2$. Unsubstituted alkyl groups are preferred.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. A lower-alkyl group may optionally have a substitution pattern as described earlier in connection with the term "alkyl". Unsubstituted lower-alkyl groups are preferred.

The term "alkoxy" refers to the group R'—O—, wherein R' is alkyl. The term "lower-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy. Alkoxy and lower-alkoxy groups may optionally have a substitution pattern as described earlier in connection with the term "alkyl". Unsubstituted alkoxy and lower-alkoxy groups are preferred.

The term "aryl" relates to the phenyl or naphthyl group, preferably the phenyl group, which can optionally be mono- or multiply-substituted by lower-alkyl, lower-alkoxy, halogen, CN, $CF_3$, hydroxy, $NO_2$, $NH_2$, N(H, lower-alkyl), N(lower-alkyl)$_2$, carboxy, aminocarbonyl, phenyl, benzyl, phenoxy, and/or benzyloxy. Preferred substituents are lower-alkyl, lower-alkoxy, halogen, CN, and/or $CF_3$.

The term "heterocycle" refers to a 5- or 6-membered ring which can comprise 1, 2 or 3 atoms selected from nitrogen, oxygen and/or sulfur such as tetrahydropyridine, dihydrofuran, dihydropyran, furyl, pyrrolyl, pyridyl, 1,2-, 1,3- and 1,4-diazinyl, thienyl, oxazolyl, oxadiazolyl, isoxazolyl, thiazolyl, isothiazolyl or imidazolyl. A heterocycle group may be optionally substituted with an aryl group or have a substitution pattern as described earlier in connection with the term "aryl".

The term "pharmaceutically acceptable salts" embraces salts of the compounds of formula (I) with inorganic or organic acids such as hydrochloric acid, hydrobromic acid, nitric acid, sulfuric acid, phosphoric acid, citric acid, formic acid, maleic acid, acetic acid, fumaric acid, succinic acid, tartaric acid, methanesulfonic acid, p-toluenesulfonic acid and the like, which are non toxic to living organisms. Preferred salts with acids are formates, maleates, citrates, hydrochlorides, hydrobromides and methanesulfonic acid salts.

The term "leaving group" relates to a group which is removed or replaced during a reaction. Examples of leaving groups are halogen, mesylate and tosylate.

In detail, the present invention relates to compounds of formula (I)

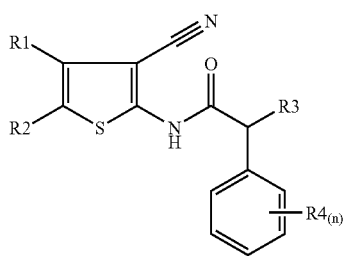

(I)

wherein
R1 and R2 are independently selected from the group consisting of lower alkyl, lower alkoxy, aminoalkyl, aryl, aralkyl, substituted lower alkyl, substituted lower alkoxy, substituted lower aminoalkyl, substituted aryl and substituted aralkyl, wherein the substituent is selected from the group consisting of one or more of halogen, hydroxy, lower alkoxy, amino, alkylamino, diaklylamino, cyano and nitro; or
R1 and R2 are taken together with the carbon atoms to which they are attached and the bond between these carbon atoms to form a 4–8 membered, substituted or unsubstituted, carbocyclic or heterocyclic ring, wherein any substituents are independently selected from the group consisting of halogen, hydroxy, lower alkyl, aryl, aralkyl, amino, alkylamino, dialkylamino, alkylsulfonyl, and alkoxycarbonyl;
R3 is selected from the group consisting of lower alkyl, substituted or unsubstituted aryl, substituted or unsubstituted aralkyl, and substituted or unsubstituted cycloalkyl, wherein any substituents are selected from the group consisting of lower alkyl, lower alkoxy, halogen, cyano, trifluoromethyl, hydroxy, nitro, amino, alkylamino, dialkylamino, carboxy, aminocarbonyl, phenyl, benzyl, phenoxy and benzyloxy; and
R4 is selected from the group consisting of lower alkyl, lower alkoxy, halogen, cyano, trifluoromethyl, hydroxy, nitro, amino, alkylamino, dialkylamino, alkylsulfonyl, and alkoxycarbonyl; and
n is 0, 1, 2, 3, 4 or 5.

In a preferred embodiment, the present invention relates to compounds of formula (I), wherein R1 and R2 are taken together with the carbon atoms to which they are attached and the bond between these carbon atoms to form a substituted or unsubstituted carbocyclic ring, wherein the substituent is preferably selected from the group consisting of one or more of halogen, hydroxy, lower alkoxy, amino, alkylamino, diaklylamino, cyano and nitro, and, more preferably, the substituent is selected from the group consisting of one or more of halogen, hydroxy, and lower alkoxy. More preferably, R1 and R2 are taken together with the carbon atoms to which they are attached and the bond between these carbon atoms to form an unsubstituted carbocyclic ring.

In another preferred embodiment, the present invention relates to compounds of formula (I) as defined above, in which R1 and R2 are taken together with the carbon atoms to which they are attached and the bond between these carbon atoms to form a substituted or unsubstituted heterocyclic ring, wherein the substituent is preferably selected from the group consisting of one or more of halogen, hydroxy, lower alkoxy, amino, alkylamino, diaklylamino, cyano and nitro, and, more preferably, the substituent is selected from the group consisting of one or more of halogen, hydroxy, and lower alkoxy. More preferably, R1 and R2 are taken together with the carbon atoms to which they are attached and the bond between these carbon atoms to form an unsubstituted heterocyclic ring.

In addition, compounds of formula (I) as defined above, wherein R3 is a cycloalkyl, represent another preferred embodiment of the present invention.

Compounds of formula (I), wherein R3 is an aryl, preferably a phenyl group, represent another preferred embodiment of the present invention.

Another preferred embodiment of the present invention relates to compounds of formula (I) as defined above, wherein R3 is a lower alkyl.

Compounds of formula (I) represent a preferred embodiment of the present invention and pharmaceutically acceptable salts of compounds of formula (I) individually also represent a preferred embodiment of the present invention.

Preferred compounds of general formula (I) are those selected from the group consisting of
N-(3-Cyano-4,5-dimethyl-thiophen-2-yl)-2,2-diphenyl-acetamide;
N-(3-Cyano-4,5-dimethyl-thiophen-2-yl)-2,3-diphenyl-propionamide;
N-(3-Cyano-4-methyl-5-ethyl-thiophen-2-yl)-2,3-diphenyl-propionamide;
N-(3-Cyano-4,7-dihydro-5H-thieno[2,3-c]pyran-2-yl)-2,2-diphenyl-acetamide;
3-Cyano-2-diphenylacetylamino-4,5,6,7-tetrahydro-5H-thieno[2,3-c]pyridine-6-carboxylic acid tert-butyl ester;
3-Cyano-2-(2-phenyl-propionylamino)-4,5,6,7-tetrahydro-5H-thieno[2,3-c]pyridine-6-carboxylic acid tert-butyl ester;
3-Cyano-2-(3-methyl-2-phenyl-butyrylamino)-4,5,6,7-tetrahydro-5H-thieno[2,3-c]pyridine-6-carboxylic acid tert-butyl ester;
3-Cyano-2-(3-methyl-2-phenyl-pentanoylamino)-4,5,6,7-tetrahydro-5H-thieno[2,3-c]pyridine-6-carboxylic acid tert-butyl ester;
N-(3-Cyano-6-methanesulfonyl-4,5,6,7-tetrahydro-thieno[2,3-c]pyridin-2-yl)-2,2-diphenyl-acetamide;
N-(3-Cyano-6-methyl-4,5,6,7-tetrahydro-thieno[2,3-c]pyridin-2-yl)-2,2-diphenyl-acetamide;
3-Cyano-2-diphenylacetylamino-4,5,6,7-tetrahydro-5H-thieno[2,3-c]pyridine-6-carboxylic acid methyl ester;
N-(3-Cyano-4,7-dihydro-5H-thieno[2,3-c]pyran-2-yl)-2-phenyl-butyramide;
3-Methyl-2-phenyl-pentanoic acid (3-cyano-5,6-dihydro-4H-cyclopenta[b]thiophen-2-yl)-amide;
3-Methyl-2-(2-phenyl-propionylamino)-(3-cyano-5,6-dihydro-4H-cyclopenta[b]thiophen-2-yl)-amide;
N-(3-Cyano-5,6-dihydro-4H-cyclopenta[b]thiophen-2-yl)-2,2-diphenyl-acetamide;
N-(3-Cyano-5,6-dihydro-4H-cyclopenta[b]thiophen-2-yl)-2-cyclopentyl-2-phenyl-acetamide;
N-(3-Cyano-5,6-dihydro-4H-cyclopenta[b]thiophen-2-yl)-2,2-diphenyl-acetamide; and
N-(3-Cyano-5,6-dihydro-4H-cyclopenta[b]thiophen-2-yl)-2-phenyl-propionamide.

Compounds of formula (I) can have one or more asymmetric carbon atoms and can exist in the form of optically pure enantiomers or as racemates. The invention embraces all of these forms.

It will be appreciated, that the compounds of general formula (I) in this invention may be derivatized at functional groups to provide derivatives which are capable of conversion back to the parent compound in vivo.

As described above, the compounds of formula (I) of the present invention may be used as medicaments for the treatment and/or prophylaxis of diseases mediated by the antagonism of the glucagon receptor. Preferably, the compounds of the present invention may be used to treat diabetes.

The invention therefore also relates to pharmaceutical compositions comprising a compound as defined above and a pharmaceutically acceptable carrier and/or adjuvant.

The compounds of formula (I) can be manufactured by the methods given below, by the methods given in the examples or by analogous methods. Appropriate reaction conditions for the individual reaction steps are known to the person skilled in the art. Starting materials are either commercially available or can be prepared by methods analogous to the methods given below or in the examples or by methods known in the art.

The following tests were carried out in order to determine the activity of the compounds of formula I.

In general, glucagon antagonists may be identified by their ability to inhibit or reduce stimulation of cAMP production, relative to the cAMP production in the presence of native glucagon alone, as determined in an adenylate cyclase assay. Adenylate cyclase assays are described, for example, by Lin et al. (Biochemistry 14:1559–1563, 1975; which is incorporated herein by reference in its entirety). Biological responses via the inositol triphosphate pathway may be assessed by measuring inositol phosphate metabolism as generally described in Subers and Nathanson (J. Mol. Cell. Cardiol. 20:131–140, 1988; which is incorporated herein by reference in its entirety) or Pittner and Fain (ibid.; which is incorporated herein by reference in its entirety) or by measuring the intracellular calcium concentration as generally described by Grynkiewicz et al. (J. Biol. Chem. 260:3440–3450, 1985; which is incorporated herein by reference in its entirety).

In a preferred embodiment, glucagon antagonists, including the 3-cyanothiophene acetamides of the present invention, may be identified through their ability to specifically inhibit the glucagon-induced adenylate cyclase response pathway. Glucagon receptors have been reported in a number of tissues, for example, liver, kidney, cardiac muscle and adipose tissue from a number of species including dog, pig, human and rat. In addition, host cells expressing recombinant glucagon receptors may also be used. Adenylate cyclase activity assays may be carried out using, for example, the method described by Lin et al. (Biochemistry. 14:1559–1563, 1975). These methods measure the level of stimulation of cAMP production relative to native glucagon and generally involve exposing a membrane preparation from tissue containing glucagon receptors to a mixture of glucagon and the glucagon antagonist in the presence of ATP. Membrane preparations from rat liver are generally used for adenylate cyclase activity assays, although other tissues containing glucagon receptors or host cells expressing a recombinant glucagon receptor may be used. Membranes may be prepared using the method described by Neville (Biochim. Biophys Acta 154:540–552, 1968) as modified by Pohl (Methods in Receptor Research, Ed. Blecher, M., New York, pp 160–164, 1976).

cAMP Measurement in CHO/GluR12B Cells

The glucagon antagonists described herein have been characterized using CHO-K1 cells overexpressing the full length human glucagon receptor (CHO/GluR 12B). Cells were plated in a 384 well plate at a density of 10000 cells/well in medium containing DMEM (Gibco #21063-029), 10% dialyzed FBS (Gibco#26400-044), 1% L-Glutamine (Gibco # 25030-081) and 1% Pen/Strep (Gibco # 15140-122). The cells were allowed to adhere overnight at 37° C. The media was removed and the cells were then pre-incubated with antagonist solubilized in DMSO diluted in DMEM containing 0.5 mM IBMX (Calbiochem #410957), 1 mg/ml BSA (Sigma #A-8806), 25 mM HEPES for 1 hr. Glucagon (0.1 nM) diluted in the same medium is then added for 30 min at 37° C. The formation of cAMP is measured in the cell lysates using a protocol and reagents purchased from Applied Biosystems for their cAMP-Screen™ System. An $IC_{50}$ of a glucagon receptor antagonist is calculated by plotting the dose response of antagonist versus the percent of maximum cAMP generated by 0.1 nM glucagon using Microsoft XLFit equation #205 (Sigmoidal Dose Response w/variable slope). Provided the appropriate concentrations of antagonist are used to obtain saturation at both the high and low concentrations, the midpoint of the curve is extrapolated as the $IC_{50}$.

The $IC_{50}$ values for the inhibition of glucagon stimulated cAMP production as measured in the above described cell based assay for each of the compounds described in the examples below are $\leq 10.0$ μM.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols.

Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1–500 mg, preferably 1–100 mg, of a compound of formula I.

The following Examples serve to illustrate the present invention in more detail. They are, however, not intended to limit its scope in any manner.

GENERAL METHODS

The compounds of formula (I) can be manufactured by the methods given below, by the methods outlined in the examples or by analogous methods.

Scheme 1, below, generally describes the synthesis of compounds of formula (I). Thiophene (b) may be formed by contacting ketone (a) with malononitrile and sulfur in an alcoholic solvent in the presence of a secondary amine. The compound of formula (I) may then be formed by contacting acetyl chloride (c) with thiophene (b).

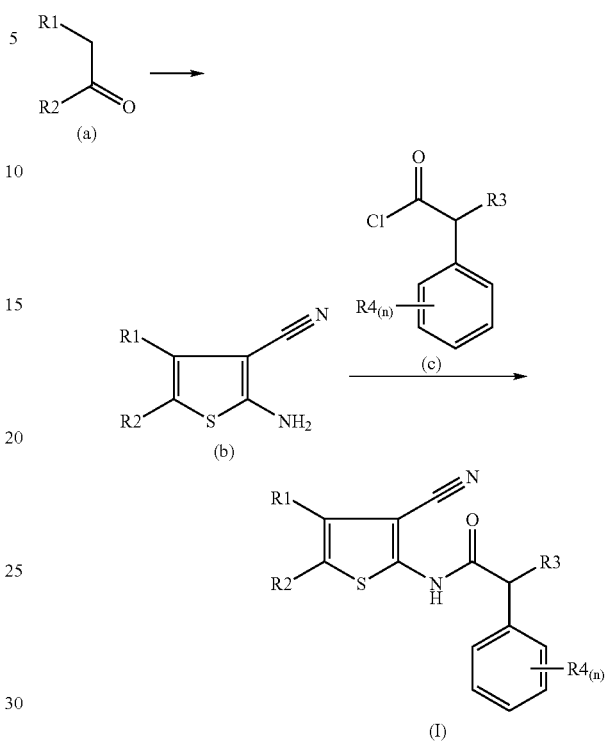

Scheme 1:

Derivatization of compounds of formula (I) may produce additional compounds within the scope of the present invention. Scheme 2, below, shows one example of various compounds produced from a t-BOC-tetrahydrothienopyridine compound (d). Removal of the t-BOC group yields the amine (e). Amine (e) may be functionalized by any method known to one of skill in the art. For example, amine (e) may be converted into an alkyl amine (f), carbamate (g) or sulfonate (h).

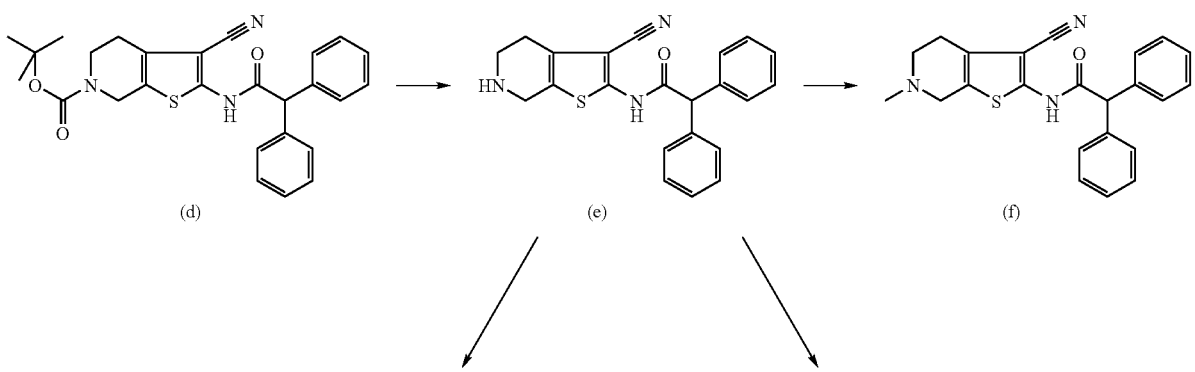

Scheme 2:

-continued

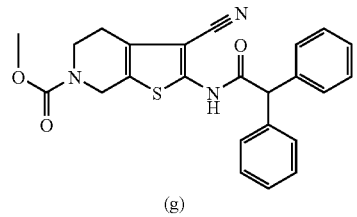

(g)

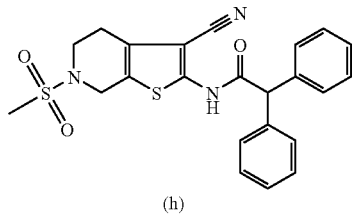

(h)

EXAMPLES

Example 1

N-(3-Cyano-4,5-dimethyl-thiophen-2-yl)-2,2-diphenyl-acetamide

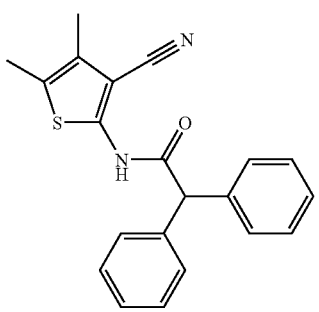

Step 1: Preparation of 2-Amino-3-cyano-4,5-dimethylthiophene.

To a stirred mixture of methylethyl ketone (4.51 mL; 50.0 mmol), malononitrile (3.34 g; 50.0 mmol) and sulfur (1.60 g; 50.0 mmol) in absolute ethanol (20 mL) under nitrogen at 0° C. was added diethylamine (5.00 mL) dropwise. The mixture was then warmed to 45–50° C. and stirred for 4 hours. The mixture was then allowed to cool to room temperature, filtered to remove insoluble material and concentrated in vacuo. The crude product was chromatographed (Merck Silica gel 60, 230–400 mesh, eluent: 20% ethylacetate/hexanes) to provide 2.35 g (31%) of 2-Amino-3-cyano-4,5-dimethylthiophene as a light brown foam.

Step 2: Preparation of N-(3-Cyano-4,5-dimethyl-thiophen-2-yl)-2,2-diphenyl-acetamide To a stirred solution of 2-Amino-3-cyano-4,5-dimethylthiophene (152 mg; 1.0 mmol) and diphenylacetyl chloride (300 mg; 1.3 mmol) in dry methylene chloride (10 mL) under nitrogen at room temperature was added triethylamine (0.42 mL; 3.0 mmol) dropwise. After 1.5 h, the mixture was washed with 1N HCl. The organic layer was dried over sodium sulfate, filtered and concentrated in vacuo. The crude product was triturated with cold 30% ethylacetate/hexanes and filtered to give 162 mg (47%) of N-(3-Cyano-4,5-dimethyl-thiophen-2-yl)-2,2-diphenyl-acetamide as a white solid. ES-HRMS m/e calcd for $C_{21}H_{18}N_2OS$ (M+H$^+$) 347.1213, found 347.1217.

Example 2

N-(3-Cyano-4,5-dimethyl-thiophen-2-yl)-2,3-diphenyl-propionamide

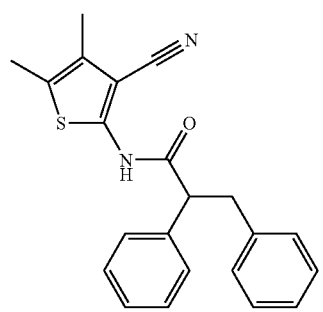

EDCI (61 mg; 0.32 mmol) was added to a solution of 2-Amino-3-cyano-4,5-dimethylthiophene (prepared in Example 1, Step 1; 24 mg; 0.148 mmol) and 2,3-diphenyl-propionic acid (72 mg; 0.32 mmol). After stirring for 19 h, the reaction mixture was applied directly to a silica gel column (Merck Silica gel 60, 230–400 mesh, eluent: 10%–33% ethylacetate/hexanes) to provide N-(3-Cyano-4,5-dimethyl-thiophen-2-yl)-2,3-diphenyl-propionamas a white solid (17.0 mg; 39%).

ES-HRMS m/e calcd for $C_{22}H_{20}N_2OS$ (M+H$^+$) 361.1369, found 361.1374.

Example 3

N-(3-Cyano-4-methyl-5-ethyl-thiophen-2-yl)-2,3-diphenyl-propionamide

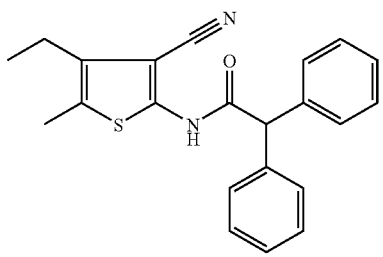

By replacing the methylethylketone of Example 1 with methylpropylketone, the compound of Example 3 may be prepared.

Example 4

N-(3-Cyano-4,7-dihydro-5H-thieno[2,3-c] pyran-2-yl)-2,2-diphenyl-acetamide

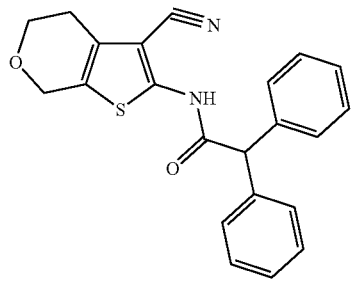

Step 1: Preparation of 2-Amino-3-cyano-4,7-dihydro-5H-thieno[2,3-c]pyran.

To a stirred mixture of dihydro-4H-pyran-4-one (5.00 g; 50.0 mmol), malononitrile (3.34 g; 50.0 mmol) and sulfur (1.60 g; 50.0 mmol) in absolute ethanol (20 mL) under nitrogen at 0° C. was added diethylamine (5.00 mL) dropwise. The mixture was then warmed to 45–50° C. and stirred for 4.5 hours. The mixture was then allowed to cool to room temperature. The solid was filtered, washed several times with cold ethanol to provide 6.09 g (68%) of 2-Amino-3-cyano-4,7-dihydro-5H-thieno[2,3-c]pyran as a tan colored solid.

Step 2: Preparation of of N-(3-Cyano-4,7-dihydro-5H-thieno[2,3-c]pyran-2-yl)-2,2-diphenyl-acetamide To a stirred solution of 2-Amino-3-cyano-4,7-dihydro-5H-thieno[2,3-c]pyran (400 mg; 2.22 mmol) and triethylamine (0.93 mL; 6.66 mmol) in dry methylene chloride (10 mL) under nitrogen at room temperature was added diphenylacetyl chloride (768 mg; 3.33 mmol). After 72 h, the mixture was diluted with methylene chloride and washed with 1N HCl. The organic layer was dried over sodium sulfate, filtered and concentrated in vacuo. The crude product was triturated with cold diethyl ether and filtered to give 310 mg (37%) of N-(3-Cyano-4,7-dihydro-5H-thieno[2,3-c]pyran-2-yl)-2,2-diphenyl-acetamide as a white solid. ES-HRMS m/e calcd for $C_{22}H_{18}N_2O_2S$ (M+H$^+$) 375.1162, found 375.1165.

Example 5

3-Cyano-2-diphenylacetylamino-4,5,6,7-tetrahydro-5H-thieno[2,3-c]pyridine-6-carboxylic acid tert-butyl ester

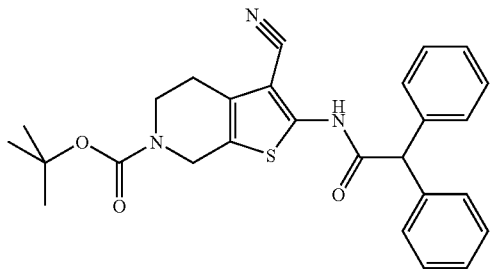

Step 1: Preparation of 2-Amino-3-Cyano-4,5,6,7-tetrahydro-5H-thieno[2,3-c]pyridine-6-carboxylic acid tert-butyl ester.

To a stirred mixture of tert-butyl 4-oxo-1-piperidinecarboxylate (15.96 g; 80.0 mmol), malononitrile (5.28 g; 80.0 mmol) and sulfur (2.56 g; 80.0 mmol) in absolute ethanol (40 mL) under nitrogen at 0° C. was added diethylamine (8.00 mL) dropwise. The mixture was then warmed to room temperature for 1 hour and then further heated to 45–50° C. for 1 h. The mixture was then allowed to cool to room temperature and an additional 10 mL of ethanol was added. The resulting slurry cooled to 0° C. and then filtered to collect the product. The product was washed three times with 10 mL of cold ethanol to provide 15.75 g (71%) of 2-amino-3-cyano-4,5,6,7-tetrahydro-5H-thieno[2,3-c]pyridine-6-carboxylic acid tert-butyl ester as a light orange colored solid.

Step 2: Preparation of 3-Cyano-2-diphenylacetylamino-4,5,6,7-tetrahydro-5H-thieno[2,3-c]pyridine-6-carboxylic acid tert-butyl ester.

To a stirred solution of 2-Amino-3-Cyano-4,5,6,7-tetrahydro-5H-thieno[2,3-c]pyridine-6-carboxylic acid tert-butyl ester (8.00 g; 28.7 mmol) and triethylamine (10.01 mL; 71.8 mmol) in dry methylene chloride (50 mL) under nitrogen at room temperature was added diphenylacetyl chloride (9.92 g; 43.0 mmol). After 18 h, the mixture was diluted with methylene chloride and washed with 1N HCl. The organic layer was dried over sodium sulfate, filtered and concentrated in vacuo. The crude product was chromatographed (eluent: 35% ethyl acetate/hexanes to give 13.60 g (100%) of 3-Cyano-2-diphenylacetylamino-4,5,6,7-tetrahydro-5H-thieno[2,3-c]pyridine-6-carboxylic acid tert-butyl ester as a foam. ES-HRMS m/e calcd for $C_{27}H_{27}N_3O_3S$ (M+H$^+$) 474.1846, found 474.1849.

Example 6

3-Cyano-2-(2-phenyl-propionylamino)-4,5,6,7-tetrahydro-5H-thieno[2,3-c]pyridine-6-carboxylic acid tert-butyl ester

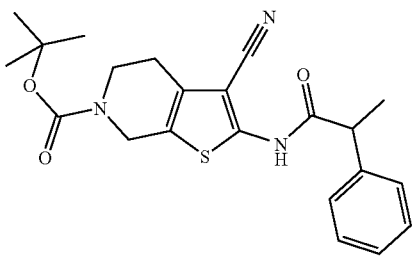

Step 1: Preparation of 2-phenylpropionyl chloride

To a stirred solution of 2-phenylpropionic acid (0.36 mL; 2.6 mmol) and a catalytic amount of dry dimethylformamide (ca. 10 μL) in 3.0 mL of dry methylene chloride under nitrogen at room temperature was added oxalyl chloride (0.34 mL; 3.9 mmol) dropwise. After 30 minutes, the mixture was concentrated in vacuo and used immediately for Step 2.

Step 2: Preparation of 3-Cyano-2-(2-phenyl-propionylamino)-4,5,6,7-tetrahydro-5H-thieno[2,3-c]pyridine-6-carboxylic acid tert-butyl ester To a stirred solution of 2-Amino-3-Cyano-4,5,6,7-tetrahydro-5H-thieno[2,3-c]pyridine-6-carboxylic acid tert-butyl ester (418 mg; 1.5 mmol; preparation outlined in Example 4, Step 1) and potassium carbonate (1106 mg; 8.0 mmol) in 10 mL of dry diethyl ether under nitrogen at room temperature was added a solution of 2-phenylpropionyl chloride (Prepared in Example 5, step 1) in 3.0 mL of dry methylene chloride. The mixture was allowed to stir for 22 h and then concentrated in vacuo. The residue was taken up into methylene chloride and washed with 10% potassium carbonate solution. The organic layer was dried over sodium sulfate, filtered and concentrated in vacuo to give 813 mg of product. Trituration with cold anhydrous diethyl ether provided 353 mg (54%) of 3-Cyano-2-(2-phenyl-propionylamino)-4,5,6,7-tetrahydro-5H-thieno[2,3-c]pyridine-6-carboxylic acid tert-butyl ester as an off white solid. ES-HRMS m/e calcd for $C_{22}H_{35}N_3O_3SNa$ (M+Na$^+$) 434.1509, found 434.1509.

Example 7

3-Cyano-2-(3-methyl-2-phenyl-butyrylamino)-4,5,6,7-tetrahydro-5H-thieno[2,3-c]pyridine-6-carboxylic acid tert-butyl ester

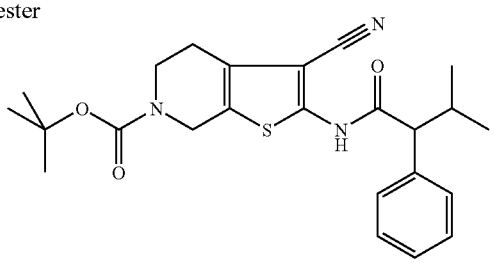

Step 1: Preparation of 3-methyl-2-phenylbutyryl chloride

To a stirred solution of 3-methyl-2-phenylbutyric acid (891 mg; 5.0 mmol) and a catalytic amount of dry dimethylformamide (ca. 10 uL) in 10 mL of dry methylene chloride under nitrogen at room temperature was added oxalyl chloride (0.65 mL; 7.5 mmol) dropwise. After 1 hour, the mixture was concentrated in vacuo and used immediately for Step 2.

Step 2: Preparation of 3-Cyano-2-(3-methyl-2-phenyl-butyrylamino)-4,5,6,7-tetrahydro-5H-thieno[2,3-c]pyridine-6-carboxylic acid tert-butyl ester Reaction of 3-methyl-2-phenylbutyryl chloride (Prepared in Example 6, Step 1) and of 2-Amino-3-Cyano-4,5,6,7-tetrahydro-5H-thieno[2,3-c]pyridine-6-carboxylic acid tert-butyl ester (836 mg; 3.0 mmol) according to the procedure outlined in Example 5 for 24 h at room temperature provided after workup, crude product which was subjected to flash chromatography (Merck Silica gel 60, 230–400 mesh; Eluent: gradient 20 to 30% ethyl acetate/hexanes) to provide 513 mg of 3-Cyano-2-(3-methyl-2-phenyl-butyrylamino)-4,5,6,7-tetrahydro-5H-thieno[2,3-c]pyridine-6-carboxylic acid tert-butyl ester as a white solid and 444 mg of recovered starting material. ES-HRMS m/e calcd for $C_{24}H_{39}N_3O_3SNa$ (M+Na$^+$) 462.1822, found 462.1825.

Example 8
3-Cyano-2-(3-methyl-2-phenyl-pentanoylamino)-4,5,6,7-tetrahydro-5H-thieno[2,3-c]pyridine-6-carboxylic acid tert-butyl ester

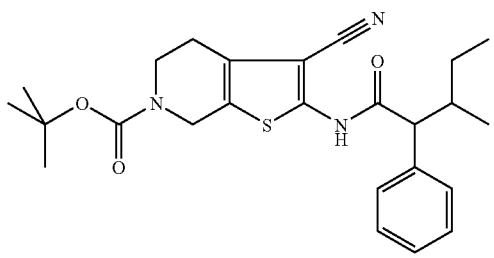

Step 1: Preparation of 3-methyl-2-phenylvaleryl chloride

To a stirred solution of 3-methyl-2-phenylvaleric acid (1.23 g; 6.2 mmol) and a catalytic amount of dry dimethylformamide (ca. 20 μL) in 5 mL of dry methylene chloride under nitrogen at room temperature was added oxalyl chloride (4.8 mL of 2.0 M solution in methylene chloride) dropwise. After 45 minutes, the mixture was concentrated in vacuo and used immediately for Step 2.

Step 2: Preparation of 3-Cyano-2-(3-methyl-2-phenyl-pentanoylamino)-4,5,6,7-tetrahydro-5H-thieno[2,3-c]pyridine-6-carboxylic acid tert-butyl ester Reaction of 3-methyl-2-phenylvaleryl chloride (Prepared in Example 7, Step1) and of 2-Amino-3-Cyano-4,5,6,7-tetrahydro-5H-thieno[2,3-c]pyridine-6-carboxylic acid tert-butyl ester (869 mg; 3.1 mmol) according to the procedure outlined in Example 5 for 15 h at room temperature provided after workup, crude which was subjected to flash chromatography (Biotage 40M; eluent: gradient 5 to 10% ethyl acetate/hexanes) to provide 597 mg of 3-Cyano-2-(3-methyl-2-phenyl-pentanoylamino)-4,5,6,7-tetrahydro-5H-thieno[2,3-c]pyridine-6-carboxylic acid tert-butyl ester as a mixture of diastereomers and 209 mg of recovered starting material. ES-HRMS m/e calcd for $C_{25}H_{31}N_3O_3SNa$ (M+Na$^+$) 476.1978, found 476.1984.

Example 9

N-(3-Cyano-6-methanesulfonyl-4,5,6,7-tetrahydro-thieno[2,3-c]pyridin-2-yl)-2,2-diphenyl-acetamide

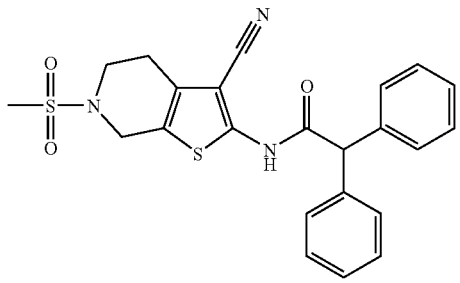

Step 1: Preparation of N-(3-Cyano-4,5,6,7-tetrahydro-thieno[2,3-c]pyridin-2-yl)-2,2-diphenyl-acetamide Trifluoroacetic acid (20 mL) was added to a stirred solution of 3-Cyano-2-diphenylacetylamino-4,5,6,7-tetrahydro-5H-thieno[2,3-c]pyridine-6-carboxylic acid tert-butyl ester (prepared in Example 4, Step 2; 13.60 g) in dry methylene chloride under nitrogen at 0° C. After 5 minutes, the mixture was allowed to warm to room temperature and stirred for 1 hr. The mixture was concentrated in vacuo and the oily residue was triturated with dry diethyl ether and filtered. The filter cake was washed with dry ether (3×100 mL) and allowed to air dry to give 14.50 g of N-(3-Cyano-4,5,6,7-tetrahydro-thieno[2,3-c]pyridin-2-yl)-2,2-diphenylacetamide as the trifluoacetate salt. Recrystallization from tetrahydrofuran/ether provided 8.75 g of of N-(3-Cyano-4,5,6,7-tetrahydro-thieno[2,3-c]pyridin-2-yl)-2,2-diphenylacetamide as the trifluoacetate salt Step 2: Preparation of N-(3-Cyano-6-methanesulfonyl-4,5,6,7-tetrahydro-thieno[2,3-c]pyridin-2-yl)-2,2-diphenyl-acetamide Methanesulfonic anhydride (90 mg; 0.517 mmol) was added dropwise to a solution of N-(3-Cyano-4,5,6,7-tetrahydro-thieno[2,3-c]pyridin-2-yl)-2,2-diphenyl-acetamide (140 mg; 0.342 mmol) and Et$_3$N (200 μL; 1.43 mmol) in CH$_2$Cl$_2$ (6 mL). After stirring for 4.5 h, the reaction mixture was diluted with ethyl acetate and washed once with water and twice with brine. The combined aqueous layers were extracted twice with ethyl acetate. The combined organic layers were dried over $Na_2SO_4$. Filtration followed by removal of all volatiles in vacuo yielded a waxy solid from which N-(3-Cyano-6-methanesulfonyl-4,5,6,7-tetrahydro-thieno[2,3-c]pyridin-2-yl)-2,2-diphenyl-acetamide (100 mg; 65%) was isolated by flash chromatography (40%–66% ethyl acetate in hexane). ES-HRMS m/e calcd for $C_{23}H_{21}N_3O_3S_2$ (M+H$^+$) 452.1097, found 452.1096.

Example 10

N-(3-Cyano-6-methyl-4,5,6,7-tetrahydro-thieno[2,3-c]pyridin-2-yl)-2,2-diphenyl-acetamide

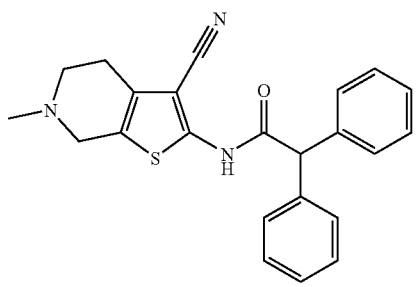

To a stirred solution of N-(3-Cyano-4,5,6,7-tetrahydro-thieno[2,3-c]pyridin-2-yl)-2,2-diphenyl-acetamide (prepared in Example 8, step 1; 75 mg; 0.15 mmol) and formaldehyde (0.1 mL of 37% solution) in dry methanol at room temperature was added sodium cyanoborohydride (14.5 mg; 0.23 mmol). The mixture was allowed to stir for 1 hour at room temperature then concentrated in vacuo. The residue was taken up into methylene chloride and washed with water. The organic layer was dried (sodium sulfate) and concentrated in vacuo to give 50 mg (85%) of N-(3-Cyano-6-methyl-4,5,6,7-tetrahydro-thieno[2,3-c]pyridin-2-yl)-2,2-diphenyl-acetamide. ES-HRMS m/e calcd for $C_{23}H_{21}N_3OS$ (M+H$^+$) 388.1478, found 388.1481.

Example 11

3-Cyano-2-diphenylacetylamino-4,5,6,7-tetrahydro-5H-thieno[2,3-c]pyridine-6-carboxylic acid methyl ester

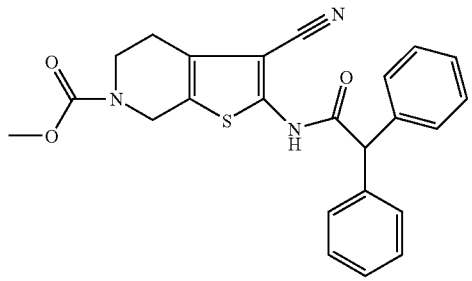

Methylchloroformate (5 μL; 0.04 mmol) was added dropwise to a solution of N-(3-Cyano-4,5,6,7-tetrahydro-thieno[2,3-c]pyridin-2-yl)-2,2-diphenyl-acetamide (20 mg; 0.06 mmol) and $Et_3N$ (200 μL; 1.43 mmol) in $CH_2Cl_2$ (6 mL). After stirring for 3.5 h, the mixture was concentrated in vacuo and the crude product purified by by flash chromatography (Merck Silica gel 60, 230–400 mesh; Eluent: gradient 50% to 66% ethyl acetate/hexanes) to provide 11 mg (64%) as an oil. ES-HRMS m/e calcd for $C_{24}H_{21}N_3O_3Sa$ (M+H$^+$) 432.1377, found 432.1381.

Example 12

3-Methyl-2-phenyl-pentanoic acid (3-cyano-5,6-dihydro-4H-cyclopenta[b]thiophen-2-yl)-amide

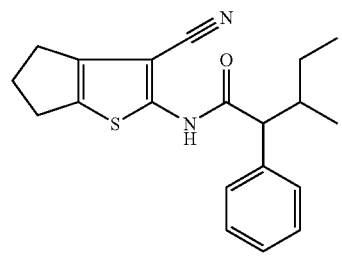

Step 1: Preparation of 2-Amino-3-cyano-5,6-dihydro-4H-cyclopenta[b]thiophene.

Diethylamine (2.50 mL) was added dropwise to a stirred solution of cyclopentanone (2.21 mL; 25.0 mmol), malononitrile (1.67 g; 25.0 mmol) and sulfur (0.80 g; 25.0 mmol) in absolute ethanol (10 mL) under nitrogen at 0° C. After 10 min., the mixture was allowed to warm to room temperature and stirred for 3 h. The mixture was then concentrated in vacuo and the crude residue was chromatographed (Merck Silica gel 60, 230–400 mesh; Eluent: 30% ethyl acetate/hexanes) to provide 1.18 g of 2-Amino-3-cyano-5,6-dihydro-4H-cyclopenta[b]thiophene as a light brown foam.

Step 2: Preparation of 3-Methyl-2-phenyl-pentanoic acid (3-cyano-5,6-dihydro-4H-cyclopenta[b]thiophen-2-yl)-amide Reaction of 3-methyl-2-phenylvaleryl chloride (Prepared in Example 7, Step1) and 2-Amino-3-cyano-5,6-dihydro-4H-cyclopenta[b]thiophene (164 mg; 1.0 mmol) according to the procedure outlined in Example 5 for 20 h at room temperature provided after workup, crude which triturated with diethylether to give 94 mg of crude 3-Methyl-2-phenylpentanoic acid (3-cyano-5,6-dihydro-4H-cyclopenta[b]thiophen-2-yl)-amide which was further purified by dissolving in methylene chloride and passing through a short plug of Merck Silica gel 60 to provide 82 mg (24%) of 3-Methyl-2-phenyl-pentanoic acid (3-cyano-5,6-dihydro-4H-cyclopenta[b]thiophen-2-yl)-amide as a mixture of diastereomers. ES-HRMS m/e calcd for $C_{26}H_{38}N_2O_2$ (M+Ht) 411.3006, found 411.3011.

Example 13

3-Methyl-2-(2-phenyl-propionylamino)-(3-cyano-5,6-dihydro-4H-cyclopenta[b]thiophen-2-yl)-amide By replacing the 3-methyl-2-phenylvaleryl chloride of Example 12 with 2-phenylpropionyl chloride, the compound of Example 13 may be prepared.

Example 14

N-(3-Cyano-5,6-dihydro-4H-cyclohexa[b]thiophen-2-yl)-2,2-diphenyl-acetamide

By replacing the cyclopentanone of Example 12 with cyclohexanone, the compound of Example 14 may be prepared

Example 15

N-(3-Cyano-5,6-dihydro-4H-cyclopenta[b]thiophen-2-yl)-2-cyclopentyl-2-phenyl-acetamide

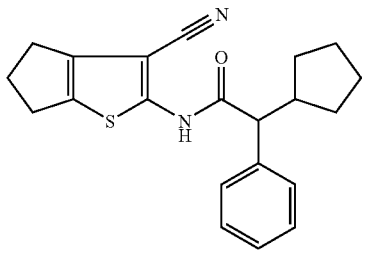

Step 1: Preparation of α-phenylcyclopentaneacetyl chloride.

To a stirred solution of α-phenylcyclopentaneacetic acid (422 mg; 2.0 mmol) and a catalytic amount of dry dimethylformamide (ca. 20 uL) in 5 mL of dry methylene chloride under nitrogen at room temperature was added oxalyl chloride (1.5 mL of 2.0 M solution in methylene chloride) dropwise. After 45 minutes, the mixture was concentrated in vacuo to give crude α-phenylcyclopentaneacetyl chloride which was used immediately for Step 2.

Step 2: Preparation of N-(3-Cyano-5,6-dihydro-4H-cyclopenta[b]thiophen-2-yl)-2-cyclopentyl-2-phenyl-acetamide Reaction of α-phenylcyclopentaneacetyl chloride (Prepared in Example 12, Step1) and 2-Amino-3-cyano-5,6-dihydro-4H-cyclopenta[b]thiophene (164 mg; 1.0 mmol) according to the procedure outlined in Example 5 for 20 h at room temperature provided after workup, crude product which triturated with diethylether to give 111 mg of which was further purified by recrystallization from ethylacetate/hexanes to provide 44 mg (%) of N-(3-Cyano-5,6-dihydro-4H-cyclopenta[b]thiophen-2-yl)-2-cyclopentyl-2-phenyl-acetamide as a light brown solid. EI-HRMS m/e calcd for $C_{21}H_{32}N_2OS$ (M+) 350.1453, found 350.1456.

Example 16

N-(3-Cyano-5,6-dihydro-4H-cyclopenta[b]thiophen-2-yl)-2,2-diphenyl-acetamide

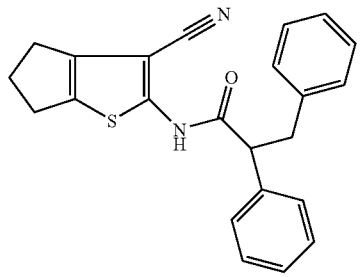

EDCI (59 mg; 0.308 mmol) was added to a solution of 2-Amino-3-cyano-5,6-dihydro-4H-cyclopenta[b]thiophene (25 mg; 0.152 mmol) and 2,3-diphenylpropionic acid (70 mg; 0.309 mmol). After stirring for 19 h, the reaction mixture was applied directly to a silica gel column (Merck Silica gel 60; eluent: 10%–33% ethyl acetate/hexanes) to provide 13.0 mg (23%) of N-(3-Cyano-5,6-dihydro-4H-cyclopenta[b]thiophen-2-yl)-2,2-diphenyl-acetamide as a white solid. EI-HRMS m/e calcd for $C_{22}H_{18}N_2OS$ (M+H+) 358.1140, found 358.1140.

Example 17

N-(3-Cyano-5,6-dihydro-4H-cyclopenta[b]thiophen-2-yl)-2-phenyl-propionamide

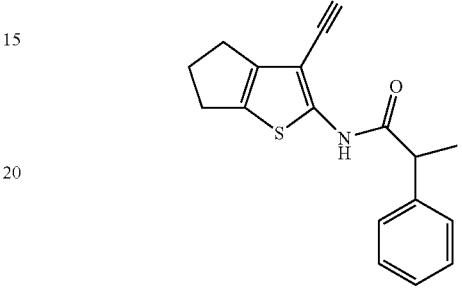

EDCI (42 mg; 0.219 mmol) was added to a solution of 2-Amino-3-cyano-5,6-dihydro-4H-cyclopenta[b]thiophene (18 mg; 0.11 mmol) and 2-phenylpropionic acid (30 μL; 0.22 mmol). After stirring for 19 h, the reaction mixture was applied directly to a silica gel column (Merck Silica gel 60; eluent: 12.5%–33% ethyl acetate/hexanes) to provide 3.5 mg (11%) of N-(3-Cyano-5,6-dihydro-4H-cyclopenta[b]thiophen-2-yl)-2-phenyl-propion as a white solid. ES-HRMS m/e calcd for $C_{17}H_{16}N_2OS$ (M+H+) 297.1056, found 297.1058.

Example 18

N-(3-Cyano-4,7-dihydro-5H-thieno[2,3-c]pyran-2-yl)-2-phenyl-butyramide

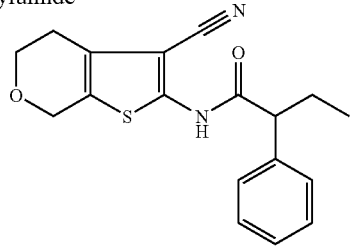

To a stirred suspension of 2-Amino-3-cyano-4,7-dihydro-5H-thieno[2,3-c]pyran (361 mg; 2.0 mmol; prepared as described in Example 2, Step 1) and potassium carbonate (1.40 g; 10.1 mmol) in diethylether (6.0 mL) was added 2-phenylbutyryl chloride dropwise. The resulting mixture was stirred at room temperature for 24 h. The solvent was then removed in vacuo, the residue taken up into methylene chloride and washed with water. The organic layer was dried (sodium sulfate) filtered and concentrated in vacuo to give crude product which was triturated with diethyl ether to provide 428 mg (66%) of N-(3-Cyano-4,7-dihydro-5H-thieno[2,3-c]pyran-2-yl)-2-phenyl-butyramide as a beige colored solid. EI-HRMS m/e calcd for $C_{18}H_{18}N_2O_2S$ (M+) 326.1809, found 326.1809.

EXAMPLES

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The amount of active compound of formula (I) in the above examples is for illustrative purposes. The actual amount of the compound of formula (I) may vary depending on the patient and intended use or effect.

It should be understood, of course, that the foregoing relates to preferred embodiments of the invention and that modifications may be made without departing from the spirit and scope of the invention as set forth in the following claims.

We claim:

1. A compound of formula (I)

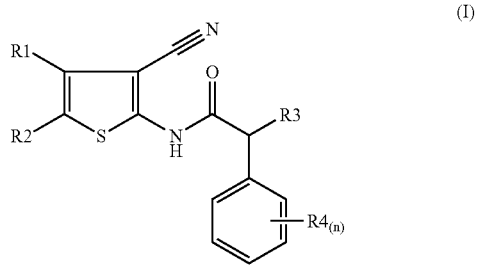

wherein
- R1 and R2 are independently selected from the group consisting of lower alkyl, lower alkoxy, aminoalkyl, aryl, aralkyl, substituted lower alkyl, substituted lower alkoxy, substituted lower aminoalkyl, substituted aryl and substituted aralkyl, wherein the substituent is selected from the group consisting of one or more of halogen, hydroxy, lower alkoxy, amino, alkylamino, diaklylamino, cyano and nitro; or
- R1 and R2 are taken together with the carbon atoms to which they are attached and the bond between these carbon atoms to form a 4–8 membered, substituted or unsubstituted, carbocyclic or heterocyclic ring, wherein any substituents are independently selected from the group consisting of halogen, hydroxy, lower alkyl, aryl, aralkyl, amino, alkylamino, dialkylamino, alkylsulfonyl, and alkoxycarbonyl;
- R3 is selected from the group consisting of lower alkyl, substituted or unsubstituted aryl, substituted or unsubstituted aralkyl, and substituted or unsubstituted cycloalkyl, wherein any substituents are selected from the group consisting of lower alkyl, lower alkoxy, halogen, cyano, trifluoromethyl, hydroxy, nitro, amino, alkylamino, dialkylamino, carboxy, aminocarbonyl, phenyl, benzyl, phenoxy and benzyloxy; and
- R4 is selected from the group consisting of lower alkyl, lower alkoxy, halogen, cyano, trifluoromethyl, hydroxy, nitro, amino, alkylamino, dialkylamino, alkylsulfonyl, and alkoxycarbonyl; and
- n is 0, 1, 2, 3, 4 or 5.

2. The compound according to claim 1, wherein R1 and R2 are taken together with the carbon atoms to which they are attached and the bond between these carbon atoms to form a 4–8 membered, substituted or unsubstituted, carbocyclic or heterocyclic ring, wherein any substituents are selected from the group consisting of halogen, hydroxy, lower alkyl, amino, alkylamino, dialkylamino, alkylsulfonyl, and alkoxycarbonyl.

3. The compound according to claim 2, wherein R1 and R2 are taken together with the carbon atoms to which they are attached and the bond between these carbon atoms to form a carbocyclic ring.

4. The compound according to claim 3, wherein R1 and R2 are taken together with the carbon atoms to which they are attached and the bond between these carbon atoms to form a cyclopentyl or a cyclohexyl ring.

5. The compound according to claim 4, wherein R3 is a substituted or unsubstituted cycloalkyl.

6. The compound according to claim 5, wherein R3 is cyclopentyl.

7. The compound according to claim 4, wherein R3 is substituted or unsubstituted aryl.

8. The compound according to claim 7, wherein R3 is phenyl.

9. The compound according to claim 4, wherein R3 is lower alkyl.

10. The compound according to claim 9, wherein R3 is selected from the group consisting of methyl, ethyl, propyl, isopropyl and sec-butyl.

11. The compound according to claim 2, wherein R1 and R2 are taken together with the carbon atoms to which they are attached and the bond between these carbon atoms to form a substituted or unsubstituted heterocyclic ring.

12. The compound according to claim 11, wherein R1 and R2 are taken together with the carbon atoms to which they are attached and the bond between these carbon atoms to form a six-membered substituted or unsubstituted heterocyclic ring containing at least one heteroatom.

13. The compound according to claim 12, wherein R1 and R2 are taken together with the carbon atoms to which they are attached and the bond between these carbon atoms to form a six-membered substituted or unsubstituted heterocyclic ring containing one heteroatom.

14. The compound according to claim 13, wherein R3 is a substituted or unsubstituted cycloalkyl.

15. The compound according to claim 14, wherein R3 is cyclopentyl.

16. The compound according to claim 13, wherein R3 is substituted or unsubstituted aryl.

17. The compound according to claim 16, wherein R3 is phenyl.

18. The compound according to claim 13, wherein R3 is lower alkyl.

19. The compound according to claim 18, wherein R3 is selected from the group consisting of methyl, ethyl, propyl, isopropyl and sec-butyl.

20. The compound according to claim 13, wherein the heterocyclic ring is substituted with a ring substituent selected from the group consisting of lower alkyl, alkylsulfonyl, alkoxycarbonyl, aryl and aralkyl.

21. The compound according to claim 20, wherein the heteroatom is a nitrogen atom.

22. The compound according to claim 21, wherein the ring substituent is attached to the nitrogen atom.

23. The compound according to claim 1, wherein R1 and R2 are independently selected from the group consisting of lower alkyl, lower alkoxy, aminoalkyl, aryl, aralkyl, substituted lower alkyl, substituted lower alkoxy, substituted lower aminoalkyl, substituted aryl and substituted aralkyl.

24. The compound according to claim 23, wherein R1 and R2 independently are lower alkyl.

25. The compound according to claim 24, wherein R3 is a substituted or unsubstituted cycloalkyl.

26. The compound according to claim 25, wherein R3 is cyclopentyl.

27. The compound according to claim 24, wherein R3 is substituted or unsubstituted aryl.

28. The compound according to claim 27, wherein R3 is phenyl.

29. The compound according to claim 24, wherein R3 is lower alkyl.

30. The compound according to claim 29, wherein R3 is selected from the group consisting of methyl, ethyl, propyl, isopropyl and sec-butyl.

31. The compound according to claim 1, wherein the compound is selected from the group consisting of:
- N-(3-Cyano-4,5-dimethyl-thiophen-2-yl)-2,2-diphenyl-acetamide;
- N-(3-Cyano-4,5-dimethyl-thiophen-2-yl)-2,3-diphenyl-propionamide; and
- N-(3-Cyano-4-methyl-5-ethyl-thiophen-2-yl)-2,3-diphenyl-propionamide.

32. The compound according to claim 1, wherein the compound is selected from the group consisting of:
- N-(3-Cyano-4,7-dihydro-5H-thieno[2,3-c]pyran-2-yl)-2,2-diphenyl-acetamide;
- 3-Cyano-2-diphenylacetylamino-4,5,6,7-tetrahydro-5H-thieno[2,3-c]pyridine-6-carboxylic acid tert-butyl ester;
- 3-Cyano-2-(2-phenyl-propionylamino)-4,5,6,7-tetrahydro-5H-thieno[2,3-c]pyridine-6-carboxylic acid tert-butyl ester;

3-Cyano-2-(3-methyl-2-phenyl-butyrylamino)-4,5,6,7-tetrahydro-5H-thieno[2,3-c]pyridine-6-carboxylic acid tert-butyl ester;
3-Cyano-2-(3-methyl-2-phenyl-pentanoylamino)-4,5,6,7-tetrahydro-5H-thieno[2,3-c]pyridine-6-carboxylic acid tert-butyl ester;
N-(3-Cyano-6-methanesulfonyl-4,5,6,7-tetrahydro-thieno[2,3-c]pyridin-2-yl)-2,2-diphenyl-acetamide;
N-(3-Cyano-6-methyl-4,5,6,7-tetrahydro-thieno[2,3-c]pyridin-2-yl)-2,2-diphenyl-acetamide;
3-Cyano-2-diphenylacetylamino-4,5,6,7-tetrahydro-5H-thieno[2,3-c]pyridine-6-carboxylic acid methyl ester; and
N-(3-Cyano-4,7-dihydro-5H-thieno[2,3-c]pyran-2-yl)-2-phenyl-butyramide.

33. The compound according to claim 1, wherein the compound is selected from the group consisting of:
3-Methyl-2-phenyl-pentanoic acid-(3-cyano-5,6-dihydro-4H-cyclopenta[b]thiophen-2-yl)-amide;
3-Methyl-2-(2-phenyl-propionylamino)-(3-cyano-5,6-dihydro-4H-cyclopenta[b]thiophen-2-yl)-amide;
N-(3-Cyano-5,6-dihydro-4H-cyclopenta[b]thiophen-2-yl)-2,2-diphenyl-acetamide;
N-(3-Cyano-5,6-dihydro-4H-cyclopenta[b]thiophen-2-yl)-2-cyclopentyl-2-phenyl-acetamide;
N-(3-Cyano-5,6-dihydro-4H-cyclopenta[b]thiophen-2-yl)-2,2-diphenyl-acetamide; and
N-(3-Cyano-5,6-dihydro-4H-cyclopenta[b]thiophen-2-yl)-2-phenyl-propionamide.

34. A pharmaceutical composition comprising:
a compound of formula (I)

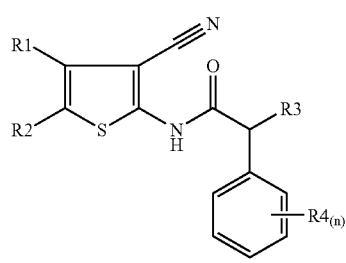

(I)

wherein
R1 and R2 are independently selected from the group consisting of lower alkyl, lower alkoxy, aminoalkyl, aryl, aralkyl, substituted lower alkyl, substituted lower alkoxy, substituted lower aminoalkyl, substituted aryl and substituted aralkyl, wherein the substituent is selected from the group consisting of one or more of halogen, hydroxy, lower alkoxy, amino, alkylamino, diaklylamino, cyano and nitro; or
R1 and R2 are taken together with the carbon atoms to which they are attached and the bond between these carbon atoms to form a 4–8 membered, substituted or unsubstituted, carbocyclic or heterocyclic ring, wherein any substituents are independently selected from the group consisting of halogen, hydroxy, lower alkyl, aryl, aralkyl, amino, alkylamino, dialkylamino, alkylsulfonyl, and alkoxycarbonyl;
R3 is selected from the group consisting of lower alkyl, substituted or unsubstituted aryl, substituted or unsubstituted aralkyl, and substituted or unsubstituted cycloalkyl, wherein any substituents are selected from the group consisting of lower alkyl, lower alkoxy, halogen, cyano, trifluoromethyl, hydroxy, nitro, amino, alkylamino, dialkylamino, carboxy, aminocarbonyl, phenyl, benzyl, phenoxy and benzyloxy;
R4 is selected from the group consisting of lower alkyl, lower alkoxy, halogen, cyano, trifluoromethyl, hydroxy, nitro, amino, alkylamino, dialkylamino, alkylsulfonyl, and alkoxycarbonyl; and
n is 0, 1, 2, 3, 4 or 5;
and pharmaceutically acceptable salts thereof; and
a pharmaceutically acceptable carrier and/or adjuvant.

35. A method for treating or preventing diseases mediated by the antagonism of the glucagon receptor, comprising:
administering to a patient in need thereof, a therapeutically effective amount of a compound of the following formula (I)

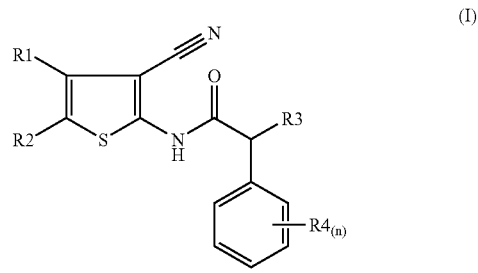

(I)

wherein
R1 and R2 are independently selected from the group consisting of lower alkyl, lower alkoxy, aminoalkyl, aryl, aralkyl, substituted lower alkyl, substituted lower alkoxy, substituted lower aminoalkyl, substituted aryl and substituted aralkyl, wherein the substituent is selected from the group consisting of one or more of halogen, hydroxy, lower alkoxy, amino, alkylamino, diaklylamino, cyano and nitro; or
R1 and R2 are taken together with the carbon atoms to which they are attached and the bond between these carbon atoms to form a 4–8 membered, substituted or unsubstituted, carbocyclic or heterocyclic ring, wherein any substituents are independently selected from the group consisting of halogen, hydroxy, lower alkyl, aryl, aralkyl, amino, alkylamino, dialkylamino, alkylsulfonyl, and alkoxycarbonyl;
R3 is selected from the group consisting of lower alkyl, substituted or unsubstituted aryl, substituted or unsubstituted aralkyl, and substituted or unsubstituted cycloalkyl, wherein any substituents are selected from the group consisting of lower alkyl, lower alkoxy, halogen, cyano, trifluoromethyl, hydroxy, nitro, amino, alkylamino, dialkylamino, carboxy, aminocarbonyl, phenyl, benzyl, phenoxy and benzyloxy;
R4 is selected from the group consisting of lower alkyl, lower alkoxy, halogen, cyano, trifluoromethyl, hydroxy, nitro, amino, alkylamino, dialkylamino, alkylsulfonyl, and alkoxycarbonyl; and
n is 0, 1, 2, 3, 4 or 5,
and pharmaceutically acceptable salts thereof.

36. The method according to claim 34, wherein said disease is diabetes.

* * * * *